(12) United States Patent
Hall

(10) Patent No.: US 12,102,744 B2
(45) Date of Patent: Oct. 1, 2024

(54) FLUID FLOW SENSING AND BUBBLE DETECTING APPARATUS AND METHOD FOR IMPROVING A FLUID FLOW SENSING AND BUBBLE DETECTING APPARATUS

(71) Applicant: MAQUET CARDIOPULMONARY GMBH, Rastatt (DE)

(72) Inventor: William F. Hall, Montclair, NJ (US)

(73) Assignee: MAQUET CARDIOPULMONARY GMBH (DE)

( * ) Notice: Subject to any disclaimer, the term of this patent is extended or adjusted under 35 U.S.C. 154(b) by 269 days.

(21) Appl. No.: 17/312,919

(22) PCT Filed: Dec. 6, 2019

(86) PCT No.: PCT/EP2019/084001
§ 371 (c)(1),
(2) Date: Jun. 10, 2021

(87) PCT Pub. No.: WO2020/120320
PCT Pub. Date: Jun. 18, 2020

(65) Prior Publication Data
US 2022/0040391 A1      Feb. 10, 2022

Related U.S. Application Data

(60) Provisional application No. 62/780,052, filed on Dec. 14, 2018.

(51) Int. Cl.
*A61M 1/36* (2006.01)
*H05K 9/00* (2006.01)
(52) U.S. Cl.
CPC ........ *A61M 1/3626* (2013.01); *A61M 1/3663* (2013.01); *H05K 9/0081* (2013.01);
(Continued)

(58) Field of Classification Search
CPC .............. A61M 1/3626; A61M 1/3663; A61M 2205/0233; A61M 2205/0238;
(Continued)

(56) References Cited

U.S. PATENT DOCUMENTS 3,974,681 A   8/1976 Namery
5,325,728 A   7/1994 Zimmerman et al.
(Continued)

FOREIGN PATENT DOCUMENTS

CN      1543654 A     11/2004
CN    101437556 A      5/2009
(Continued)

OTHER PUBLICATIONS

International Search Report and Written Opinion for International Application No. PCT/EP2019/084001, mailed Feb. 27, 2020.
(Continued)

*Primary Examiner* — Judy Nguyen
*Assistant Examiner* — James Split
(74) *Attorney, Agent, or Firm* — Frost Brown Todd LLP

(57) ABSTRACT

A fluid flow sensing and bubble detecting apparatus, comprising: —housing provided with a cavity configured to receive a tube through which conductive fluid flows; —a fluid flow sensing and bubble detecting electrical sensor assembly supported by the housing and configured to sense the flow of the fluid flowing through the tube and to detect bubbles in the fluid; and—an electrically grounded Electro-Magnetic Interference (EMI) shielding arranged between at least a part of the sensor assembly and the cavity such that the EMI shielding protects the sensor assembly from unwanted EMI emanating from a tube received within the cavity, which might otherwise cause the fluid flow sensing and bubble detecting apparatus to generate false bubble detection signals.

20 Claims, 4 Drawing Sheets

(52) U.S. Cl.
CPC ............... *A61M 2205/0233* (2013.01); *A61M 2205/0238* (2013.01); *A61M 2205/3334* (2013.01); *A61M 2205/3368* (2013.01); *A61M 2205/3375* (2013.01)

(58) Field of Classification Search
CPC .. A61M 2205/3317; A61M 2205/3334; A61M 2205/3368; A61M 2205/3375; A61M 2205/3372; H05K 9/0081
See application file for complete search history.

(56) References Cited

U.S. PATENT DOCUMENTS

| | | | |
|---|---|---|---|
| 5,368,554 | A | 11/1994 | Nazarian et al. |
| 5,583,299 | A * | 12/1996 | Murase ................ A61B 5/0265 73/861.12 |
| 6,776,758 | B2 * | 8/2004 | Peszynski ................ A61B 8/12 600/437 |
| 8,353,839 | B2 | 1/2013 | Scheirer et al. |
| 8,919,208 | B2 * | 12/2014 | Murakami .............. G01F 1/667 73/861.27 |
| 10,029,051 | B2 * | 7/2018 | Nakanishi ......... A61M 5/14228 |
| 2003/0186602 | A1 | 10/2003 | Millas et al. |
| 2003/0225324 | A1 | 12/2003 | Anderson et al. |
| 2004/0073118 | A1 | 4/2004 | Peszynski et al. |
| 2005/0197550 | A1 | 9/2005 | Al-Ali et al. |
| 2011/0009800 | A1 * | 1/2011 | Dam ...................... G01N 29/02 210/90 |
| 2013/0079609 | A1 | 3/2013 | Besko |
| 2013/0079611 | A1 | 3/2013 | Besko |
| 2014/0051956 | A1 | 2/2014 | Dalene et al. |
| 2014/0216158 | A1 * | 8/2014 | Sanabria Martin .... G01N 29/06 73/588 |
| 2014/0260644 | A1 | 9/2014 | Sahagen |
| 2018/0110913 | A1 | 4/2018 | Loderer et al. |

FOREIGN PATENT DOCUMENTS

| | | |
|---|---|---|
| CN | 101692976 A | 4/2010 |
| CN | 105188798 A | 12/2015 |
| JP | H06205772 A * | 7/1994 |
| JP | 2003033353 A * | 2/2003 |
| RU | 175583 | 12/2017 |

OTHER PUBLICATIONS

Chinese Second Office Action and Supplementary Search Report dated Apr. 18, 2024, for Application No. 201980089541.7, 6 pages.

* cited by examiner

FLUID FLOW SENSING AND BUBBLE DETECTING APPARATUS AND METHOD FOR IMPROVING A FLUID FLOW SENSING AND BUBBLE DETECTING APPARATUS

This application is a national stage application under 35 U.S.C. § 371 of international application PCT/EP2019/084001, filed Dec. 6, 2019, which claims the benefit of priority to U.S. provisional patent application Ser. No. 62/780,052, filed Dec. 14, 2018.

FIELD OF THE DISCLOSURE

The present disclosure generally relates to a fluid flow sensing and bubble detecting apparatus, which is used to determine the flow rate of a fluid flowing in a tube and detect the presence of bubbles in the fluid. The present disclosure in particular relates to fluid flow rate measuring and gas bubble detecting apparatuses, which are used to determine the flow rate of blood flowing through a tube within the extracorporeal circuit of a Heart-Lung Machine (HLM) and to detect gas bubbles in the blood flow.

BACKGROUND OF THE DISCLOSURE

U.S. Pat. No. 8,353,839 B2 to Scheirer et al. discloses an ultrasonic probe comprising an ultrasonic transducer array, which is moved to produce scans from the inside of a patient. To accomplish this, the probe is insertable into a cavity of the patient. An array of sensors is located in a fluid chamber on the distal tip of the probe and it is enclosed by an acoustic window end cap. The acoustic window cap is coated with a thin conductive layer on the inside of the window, which shields the transducer and its motive mechanism from EFI/RFI emissions.

Fluid flow rate measuring and gas bubble detecting apparatuses may be used in medical procedures such as those using extracorporeal blood circuits and systems, more specifically cardiopulmonary systems and procedures involving the bypassing of blood to and/or from the heart in an extracorporeal circuit of a Heart-Lung Machine (HLM) via pumps replacing all or a portion of the pumping activity typical of a beating heart.

U.S. Pat. No. 3,974,681 to Namery discloses an apparatus for detecting gas or gas bubbles traveling in a hollow, flexible feeding tube. More particularly, it discloses an ultrasonic bubble detector using through-transmission detection. The sensor comprises two halves with a semi-circular surface into which the tube may be placed, the two halves locking the tube between themselves. Ultrasonic transducers are positioned on both sides of the tube. Metal sound pipes are placed between the transducers and the tube to transport ultrasonic signals between the tube and the transducers. One side of the disc transducers may be grounded with a wire. A circuit for a transducer acting as emitter and a separate circuit for a transducer acting as receiver is required.

To enable not only bubble detection, as in the Namery reference, but also flow detection and to improve accuracy, more recent publications relate to multiplexing transducers, so that ultrasonic sensor elements may interchangeably be employed as detector and receiver. One example of such an apparatus is disclosed in US Patent Application Publication US 2018/0110913 A1 to Loderer et al., which is incorporated herein by reference in its entirety. Therein, in one embodiment, a fluid flow rate measuring circuit is gated on for operation by the multiplexer for a predetermined time by a processor. Energy in an ultrasonic frequency range is supplied by a generator to an ultrasonic sensor element that is to be the transmitter element to be transmitting to the opposing other ultrasonic sensor element serving as the receiver element, and then vice versa.

The fluid flow rate measuring and gas bubble detecting apparatuses disclosed in the Loderer reference represent a clear improvement over the legacy ultrasonic bubble detectors such as the one taught by the Namery reference. The apparatuses devised by Loderer can measure the fluid flow rate on top of detecting gas bubbles. Furthermore, the processing circuits are simplified compared to Namery.

However, recent tests of the Loderer apparatuses have revealed that these apparatuses are not fully reliable when used during surgical procedures involving electro-surgery. In these types of procedures, an electro-surgical unit generates a high-energy radio frequency (RF) output, which is coupled into a conductive scalpel. The surgeon uses the conductive scalpel to cut and cauterize a patient's tissue during the surgery. The carrier frequency of the RF signal generated is generally 500 KHz. The modulated waveform generated is rich in higher frequency harmonics so RF Interference (or RFI) is transmitted within the immediate surgical environment. The RFI has so far been considered to be of no concern to bubble detection sensors. Indeed, such sensors are located remote from the conductive scalpel during surgery and are not in contact with the patient. The RFI should thus be unable to reach the sensors. Tests and past experience with the Namery-type bubble sensors have never shown any sensor problems related to RFI during electro-surgery.

It now turns out that, during electro-surgery, the new Loderer-type sensors start detecting bubbles in the blood flow that are actually not there. These false positives are unacceptable during surgery and are believed to be the result of RF Interference.

SUMMARY OF THE DISCLOSURE

In light of the aforementioned, it is one object of the present disclosure to provide a flow sensing and bubble detecting apparatus, which works reliably in the presence of Electro-Magnetic Interference or EMI. In particular, the flow sensing and bubble detecting apparatus should not be influenced by RFI generated during electro-surgery even when it employs efficient multiplexing technology.

According to one broad aspect of the present disclosure, there is provided a fluid flow sensing and bubble detecting apparatus, comprising a housing provided with a cavity configured to receive a tube through which fluid flows, a fluid flow sensing and bubble detecting electrical sensor assembly supported by the housing and configured to sense the flow of fluid flowing through the tube and to detect bubbles in the fluid, and an electrically grounded Electro-Magnetic Interference—EMI—shielding arranged between at least a part of the sensor assembly and the cavity such that it protects the sensor assembly from unwanted EMI emanating from a tube received within the cavity.

By providing an EMI shielding between at least a part of the sensor assembly and the cavity, RFI originating from electro-surgery can no longer impair the proper working of the sensing apparatus.

Indeed, the present inventor surprisingly found out that the RFI generated by electro-surgery is coupled by both electrical conduction and radiation into the extracorporeal tubes, which carry the patient's blood during the surgery. Since the blood is conductive, this in-turn induces RF currents that flow within the tubes. A fluid flow and bubble detection sensor, which is attached to one of the tubes, can thus pick up the RF noise carried within the conductive blood flowing within the tube.

Due to the EMI shielding of the present disclosure, the RF noise carried via the tube to the fluid flow and bubble detection sensor does not interfere with the proper operation of the sensor.

The present inventor has discovered that, in the old Namery-type bubble sensors, one of the two electrodes of the sensor's transducers, which electrode is grounded, effectively acts as an EMI shielding. Unwittingly, in the old Namery-type bubble sensors, the grounded electrodes in the transducers double as an EMI shielding. This is why there is no false bubble detection during electro-surgery when using the old Namery-type bubble sensors.

Due to design constraints, in the new Loderer-type sensors, none of the transducers' electrodes are grounded. Unintentionally, this has the effect of stripping the sensor of its de facto EMI shielding provided by grounded electrodes.

As a result of this investigation, the present inventor decided to devise a new separate EMI shielding to eliminate the erroneous bubble detection in combined fluid flow and bubble detection sensors.

In one embodiment, the EMI shielding is a device separate from the fluid flow sensing and bubble detecting electrical sensor assembly. The EMI shielding may be an electrically conductive layer. The electrically conductive layer may be connected via an electrically conductive path with an electrically grounded portion of the housing. In this case, the electrically conductive path may be made of a portion of the layer itself, applied over a portion which itself is an electrically grounded portion of the housing.

The electrically conductive layer may be a metal foil, a vapor deposited metal or a crosshatch pattern of metallic traces. The thickness of the layer may be 1 to 20 micrometers, in particular 1 to 10 micrometers, and in one embodiment 2 to 3 micrometers. In one embodiment, the electrically conductive layer may be made of aluminum. In other embodiments, the electrically conductive layer may be made of copper, nickel, another metal or another conductive material.

In a further embodiment, the apparatus may be dedicated to a biomedical use, such as the monitoring of the flow of blood or of other biomedical fluids. The medical monitoring of flow and/or detection of bubbles may be applied to cardiopulmonary bypass applications, such as when operating heart-lung machines, extracorporeal membrane oxygenation (ECMO) systems, and/or pump-assisted lung protection (PALP) systems, and it may be applied to dialysis applications.

More generally, the EMI shielding may be applied to any probe, sensor or monitor of conductive fluids, which emanate from a patient being subjected to Electro-Surgery. The EMI shielding will be useful for any probe, sensor or monitor containing electronic circuits, which are sensitive to and may malfunction or exhibit unwanted behavior in the presence of RFI (Radio Frequency Interference) transmitted via the conductive fluid. Types of sensors, probes or monitors that may benefit from the EMI shielding, may include but are not limited to temperature, pressure, and arterial and venous blood gas monitoring.

The electrically conductive layer may be covered with a protective coating. In one embodiment, the protective coating is a dielectric protective coating. The protective coating may be made of, for example, acrylic, silicone, polyurethane or a combination of materials.

In one embodiment, the sensor assembly comprises at least one electromechanical transducer element, wherein each transducer element is electrically isolated from the apparatus's electrical ground and thus is electrically floating.

The sensor assembly may further comprise a temperature sensor. In this case, the EMI shielding may have a temperature sensor gap allowing unimpeded temperature measurements by the temperature sensor.

According to another broad aspect of the present disclosure, there is provided an apparatus for fluid flow and bubble detection, comprising a housing, in which a first sidewall, a second sidewall and a bottom wall constitute three walls of a channel, which is configured to receive a tube. The tube may be an elastic tube configured to receive a flow of liquid such as blood. The apparatus comprises a first window located in the first sidewall and a second window located in the second sidewall, and the second window may be located opposite of the first window. Behind the first window and the second window, that is, inside of the housing facing the window but covered by it, is a first ultrasonic transducer and a second ultrasonic transducer, respectively. Each of the first and second ultrasonic transducers is operable as a transmitter and as a receiver. The windows are completely or partially covered with a layer made of an electrically conductive material on a face side of the windows facing the channel. If partially covered, the size of the gaps of non-coverage are preferably limited to no more than one-quarter wavelength of the interfering RF signal. The windows allow passage of ultrasonic vibrations.

By providing the layer of conductive material, the transducers are shielded against electromagnetic interference. The layer may be applied onto the windows, which are a portion of the apparatus that is accessible from the outside without having to open the housing. The electrically conductive layer may in one embodiment be a vapor deposited layer of metal, such as aluminum. In another embodiment, the electrically conductive layer may be a metal foil. Either way, the electrically conductive layer can be applied without dismantling or destroying the housing. The electrically conductive layer may even be applied to an existing apparatus that may already have been in use. The electrically conductive layer may also be contemplated in a late design phase of an apparatus for fluid flow and bubble detection to allow protection of the transducers after most of the steps of the design and production have already been implemented. It is not required to adapt the production process to incorporate static protection in or on the sensors in the housing.

In one embodiment, the layer of conductive material is covered on a side facing the channel with a protective coating. The protective coating may be 1 to 50 micrometers, in particular 5 to 40 micrometers, and in one embodiment 10 to 30 micrometers thick.

According to another broad aspect of the present disclosure, there is provided a method of adapting an apparatus for fluid flow and bubble detection, which comprises the steps of providing an apparatus comprising a housing, in which a first side wall, a second side wall and a bottom wall constitute three walls of a channel, which is configured to receive a tube, a first window located in the first side wall, a second window located in the second side wall, a first ultrasonic transducer, operable as a transmitter and as a receiver, placed in the housing behind the first window, a second ultrasonic transducer, operable as a transmitter and receiver, placed in the housing behind the second window, and applying a layer of electrically conductive material on a face side of the windows facing the channel, wherein the face side of the windows is completely or partially covered by the layer of electrically conductive material. If partially covered, the size of the gaps of non-coverage are preferably limited to no more than one-quarter wavelength of the interfering RF signal.

According to another broad aspect of the present disclosure, there is provided a method of protecting a fluid flow sensing and bubble detecting apparatus against Electro-Magnetic Interference (or EMI), wherein the fluid flow sensing and bubble detecting apparatus is configured to receive a tube through which fluid flows and includes a fluid flow sensing and bubble detecting electrical sensor assembly configured to sense the flow of fluid flowing through a tube received in the fluid flow sensing and bubble detecting apparatus and to detect bubbles in the fluid, the method comprising the steps of fitting the fluid flow sensing and bubble detecting apparatus with a dedicated EMI shielding to protect the sensor assembly from unwanted EMI emanating from a tube received in the fluid flow sensing and bubble detecting apparatus, which EMI shielding is a device separate from the fluid flow sensing and bubble detecting electrical sensor assembly, and grounding the EMI shielding.

According to another broad aspect of the present disclosure, there is provided a fluid flow sensing and bubble detecting apparatus, comprising: a housing, in which a first side wall, a second side wall and a bottom wall constitute three walls of a channel, which is configured to receive a tube; a first window located in the first side wall; a second window located in the second side wall; a first ultrasonic transducer, operable as an ultrasonic transmitter and as an ultrasonic receiver, placed in the housing behind the first window; a second ultrasonic transducer, operable as an ultrasonic transmitter and as an ultrasonic receiver, placed in the housing behind the second window; a circuit board in electrical connection and in signal transferring connection with the transducers, wherein the circuit board is configured to control the transducers as ultrasonic transmitters and receivers, wherein the circuit board is located under the bottom wall; a first electrically conductive layer located on the side of the first window facing the channel, wherein the first electrically conductive layer is electrically grounded; and a second electrically conductive layer located on the side of the second window facing the channel, wherein the second electrically conductive layer is electrically grounded.

In one embodiment, the fluid flow sensing and bubble detecting apparatus further comprises a third ultrasonic transducer, operable as an ultrasonic transmitter and as an ultrasonic receiver, placed in the housing behind the first window, and a fourth ultrasonic transducer, operable as an ultrasonic transmitter and as an ultrasonic receiver, placed in the housing behind the second window. In this embodiment, the first ultrasonic transducer is located diagonal to the fourth ultrasonic transducer, the second ultrasonic transducer is located diagonal to the third ultrasonic transducer, the circuit board is also in electrical connection and in signal transferring connection with the third and fourth ultrasonic transducers, and the circuit board is further configured to control the third and fourth ultrasonic transducers as ultrasonic transmitters and receivers.

In one embodiment, the circuit board is essentially planar and oriented parallel to the bottom wall.

An infrared (IR) temperature sensor may be mounted on the circuit board, wherein a light sensitive side of the infrared temperature sensor faces the bottom wall.

In one embodiment, an electrically conductive layer is located between the circuit board and the bottom wall, and is placed adjacent to the circuit board. The electrically conductive layer between the circuit board and the bottom wall may comprise a separating spacer material on the underside of the electrically conductive layer between the circuit board and the bottom wall to ensure it does not short-circuit any of the electrically active elements on the circuit board. In one embodiment, the separating spacer material is conductive and in electrical connection with a portion of the housing that is electrically grounded. The separating spacer material may be, for example, aluminum, copper, nickel, another metal or another conductive material. In addition, the separating spacer material may be, for example, vacuum deposited.

BRIEF DESCRIPTION OF THE DRAWINGS

The disclosure will now be described by way of example only, with reference to the accompanying drawings, in which.

DETAILED DESCRIPTION OF THE DISCLOSURE

Figure 1:
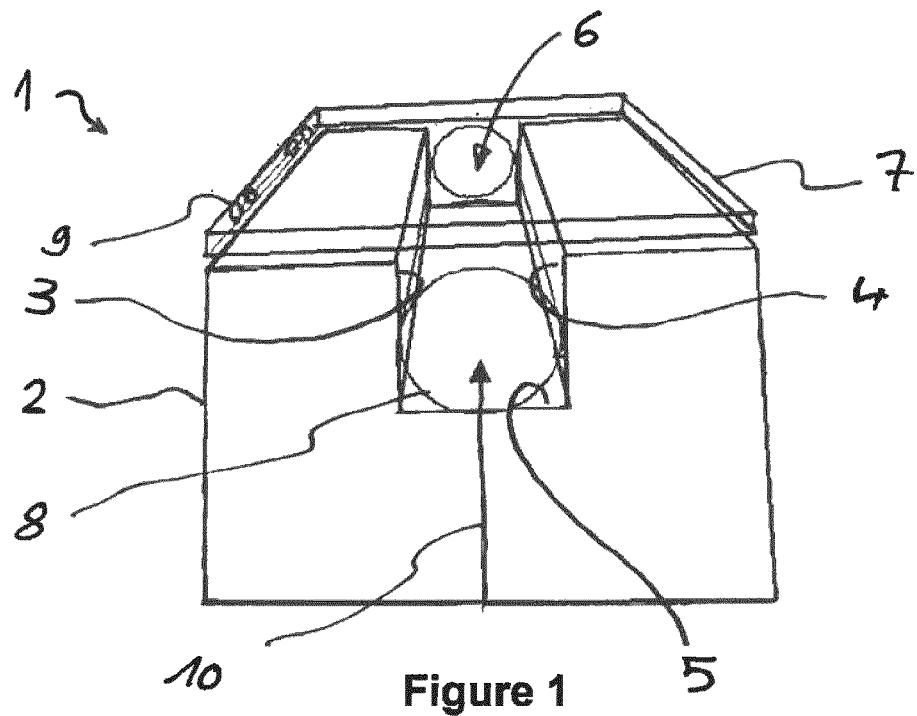
FIG. 1 shows a perspective view of an apparatus for fluid flow sensing and bubble detection, with a housing, a channel therein receiving a tube and a sensor cover covering the channel for holding the tube in place.

FIG. 1 depicts schematically an apparatus 1 for fluid flow and bubble detection, comprising a housing 2, in which a first sidewall 3, a second sidewall 4 and a bottom wall 5 constitute three walls of a channel 6, which is configured to receive a tube 8 through which a conductive liquid may flow, such as blood. The channel 6 defines a cavity. The first sidewall 3 and the second sidewall 4 face each other with the tube 8 placeable between them. In the drawings, some elements such as the housing are see-through to allow the viewer to see the elements placed therein. In practice, the actual apparatus is made of solid materials such as metal and plastic. Housing 2 may comprise or consist of aluminum.

A sensor cover 7 is adapted to enclose the tube 8. The sensor cover 7 may be made from, for example, metal or plastic material (such as polycarbonate (e.g., LEXAN)). In the non-limiting embodiment shown in FIG. 1, the sensor cover 7 is connected to the housing 2 via a hinge 9 and held in place and shut with a latch (not shown). The apparatus 1 is adapted to measure the flow rate of a fluid flow 10. It is also configured to detect gas bubbles in the fluid flow. In the present embodiment, this is done by means of ultrasonic emitters/receivers as shall be explained in conjunction with FIGS. 2 to 6.

Figure 2:
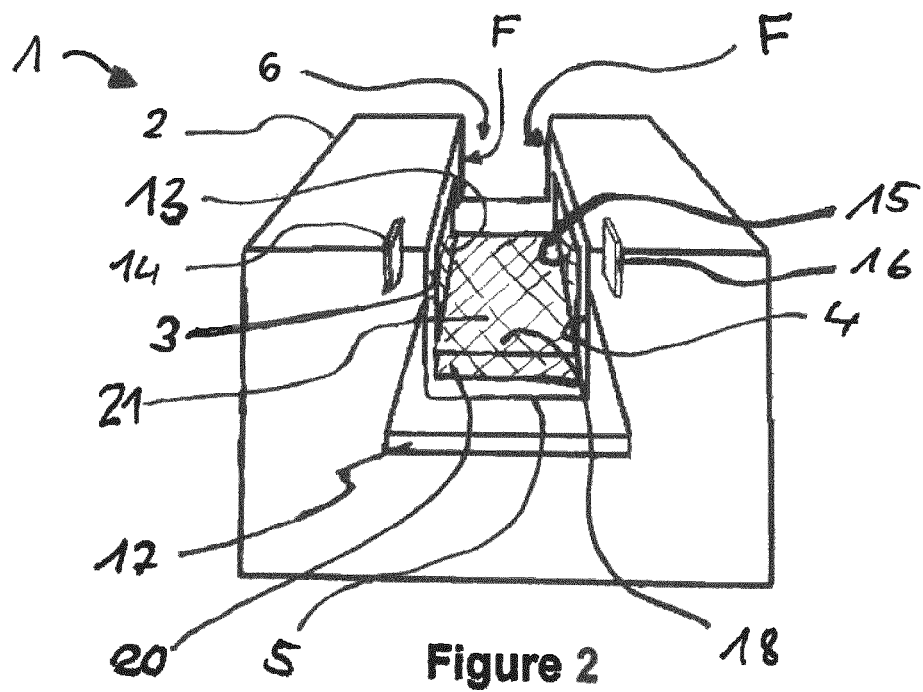
FIG. 2 shows a fluid flow sensing and bubble detection apparatus with a housing and a circuit board placed therein, which is in electrical connection with and adapted to control two transducers.

FIG. 2 shows the housing 2 without the sensor cover 7. Located in the channel 6 of the housing 2, more specifically in the first sidewall 3, is a first window 13, with a face side F facing the channel 6 or the tube 8, respectively, if it is placed into the channel 6 as depicted in FIG. 1. In the second sidewall 4, there is a second window 15. The second window 15 also has a face side F facing the channel 6 or the tube 8, if it is placed into the channel as depicted in FIG. 1.

Figure 8:
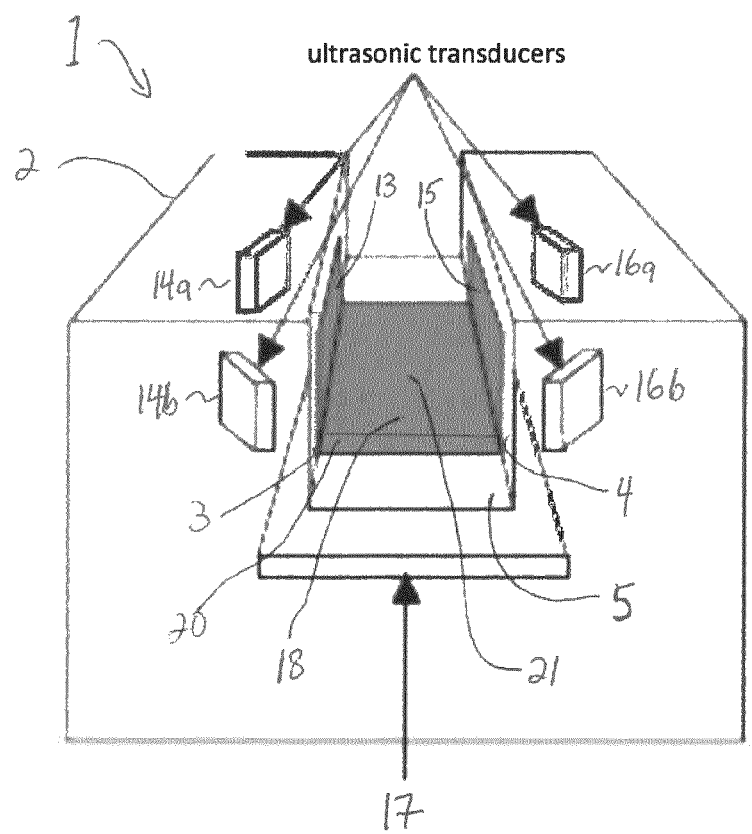
FIG. 8 shows a fluid flow sensing and bubble detection apparatus with a housing and a circuit board placed therein, which is in electrical connection with and adapted to control four transducers, which are positioned in a diagonal configuration.

The windows 13 and 15 may be completely or substantially made of a plastic material such as polymethylmethacrylate (PMMA), or other suitable acrylic or plastic, allowing ultrasonic waves to pass from ultrasonic transducers 14 and 16 through the windows 13, 15 and into the fluid flow 10 in the tube 8. Although this disclosure speaks of individual transducers 14 and 16, there may be an array or plurality of transducers on each side of the channel 6. For example, in the non-limiting embodiment shown in FIG. 8, there are four transducers (14a, 14b, 16a, 16b) positioned in a diagonal configuration with two transducers 14a, 14b located behind the first window 13, and two transducers 16a, 16b located behind the second window 15. In FIG. 8, transducer 14a is located diagonal to transducer 16b, and transducer 14b is located diagonal to transducer 16a. In this disclosure, the transducers 14 and 16 may be embodied as piezoelectric elements.

The ultrasonic transducers 14 and 16 may be operated in a multiplexed manner to sense the fluid flow 10 and detect bubbles therein. Electronic components on a circuit board 17 control the operation of the transducers 14 and 16. The circuit board 17 is placed in the housing 2 under the bottom window 18 (which is located in the bottom wall 5), preferably parallel to the bottom wall 5.

The transducers 14 and 16 and the circuit board 17 together form a fluid flow sensing and bubble detecting electrical sensor assembly supported by the housing 2.

In a way not shown in the drawings, the apparatus 1 may be utilized to sense fluid flow and detect bubbles in an extracorporeal tube bypassing, for instance, the heart and/or lungs of a patient. The patient may be operated on with an electrosurgical unit generating a radio frequency at, for example, around 500 KHz. There may be peaks at an overlaying higher frequency getting close to the frequency of the ultrasonic transducers. Electric currents induced by the electro-surgery travel through the blood in the tube and may cause Electro-Magnetic Interference (or EMI). This is prevented by an EMI shielding 21. In the non-limiting embodiments shown in FIGS. 2 and 8, the EMI shielding is an electrically conductive layer 21 deposited on each of the first window 13, the second window 15, and the bottom window 18. Layer 21 may be made of aluminum.

The conductive layer 21 is grounded. In one embodiment, grounding can be achieved by extending the layer 21 over a portion of the housing 2 that is electrically grounded, thus establishing an electrical grounding path 20. In this case, the path 20 of the layer 21 is a portion of the layer 21, which overlaps the bottom window 18, and also extends over a grounded portion of the housing 2 that is electrically conductive and connected with the rest of the housing 2.

Figure 3:
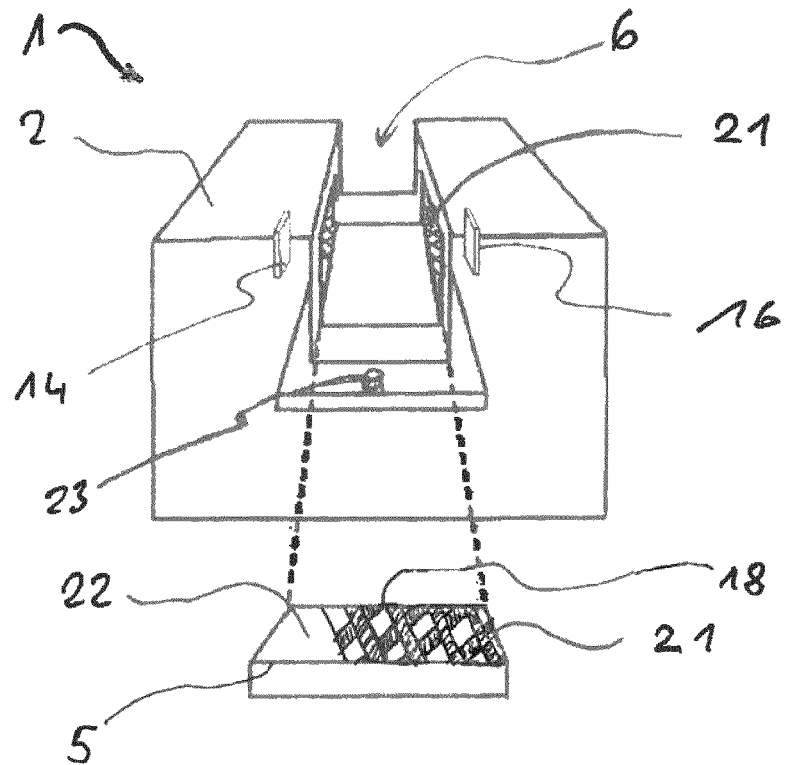
FIG. 3 shows a fluid flow sensing and bubble detection apparatus with a channel consisting of two side windows and a bottom window, the bottom window being covered with a layer of conductive material applied partially.

FIG. 3 shows a further non-limiting embodiment. In FIG. 3, the bottom wall 5 is enlarged on the bottom of the figure to illustrate more closely what it comprises. Bottom wall 5 includes an electrically conductive layer 21 that is grounded against a portion of the housing 2 or in another electrically suitable fashion. The layer 21 itself may be, for example, around 3 to 5 micrometers thick. It may be vapor deposited metal. Placed over this electrically conductive layer 21 is a protective dielectric coating 22, which preferably covers all of the surface of the electrically conductive layer 21 of the bottom wall 5. The protective coating 22 may serve to protect the vapor deposited metal coating layer 21 from erosion caused, e.g., by agents used to clean the apparatus 1. The protective coating 22 may also serve to protect the vapor deposited metal coating layer 21 from erosion caused by mechanical scrubbing to clean the apparatus 1. Furthermore, the protective coating 22 may also serve to protect the vapor deposited metal coating layer 21 from scratches during cleaning of the apparatus 1 and during placement of the tube into the channel 6.

The protective coating 22 may be thicker than the vapor deposited layer 21, for instance, the protective coating 22 may be 7 to 30 micrometers thick when the conductive layer 21 is no more than around 5 micrometers thick. This is still relatively thin, even when considering both layers, so the layer 21 and the protective coating 22 do not noticeably affect ultrasonic waves travelling through the side windows 13 and 15 to reach piezo transducers 14 and 16. The layer 21 and protective coating 22 may be applied to the side windows 13, 15, as well as the bottom window 18. The layer 21 may be made of aluminum. The coating 22 may be made of acrylic, silicone, polyurethane, or a combination of dielectric materials.

The electrically conductive layer 21 shields the transducers 14 and 16 from EMI, and, in particular, Electro-Surgical Interference (ESI). Without the ESI shielding 21, the ESI can interfere with the operation of the transducers 14, 16, which can cause false bubble detections, that is, detections of bubbles that do not exist. Various tests conducted by the applicant have proven this. In other words, application of ESI shielding 21 to a Loderer-type sensor (i.e., a flow measuring and bubble detecting sensor employing paired ultrasonic transducers and a multiplexing circuit) substantially mitigates and/or eliminates false bubble detection signals due to ESI.

Alternatively, still referring to the bottom portion of FIG. 3, showing an enlarged view of the bottom window 5, the layer 21 may be a metal foil. The foil may comprise an adhesive side that is placed facing the bottom window 18 so that the foil sticks to the window 18.

In a further variant, the windows 13, 15, 18 may be laminated structures. In this case, the EMI shielding 21 could be embedded within the windows 13, 15, 18 as a grounded conductive layer within the laminate.

In another further variant, the electrically conductive layer 21 is located on the inside of the windows 13, 15, 18 (opposite the channel 6) and in front of the transducers 14, 16, while being properly grounded (e.g., in electrical connection with a grounded portion of the housing 2).

Figure 4:
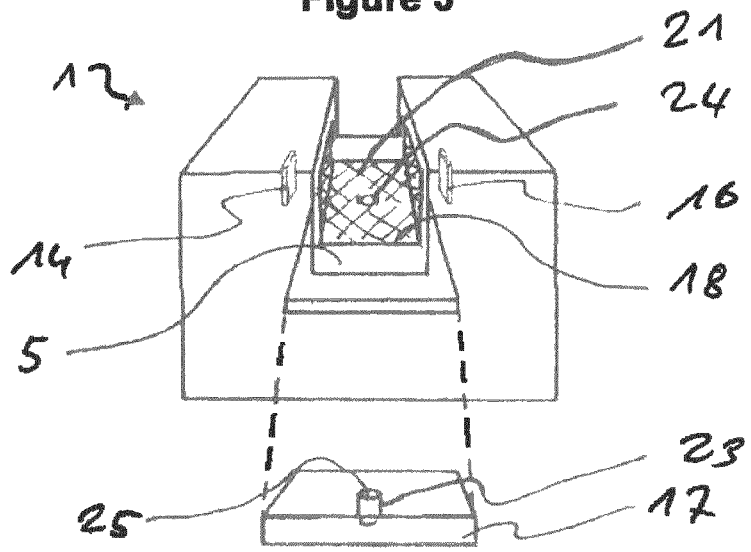
FIG. 4 shows a fluid flow and bubble detection apparatus with a channel consisting of two side windows and a bottom window, the bottom window being covered with a layer of conductive material applied partially, leaving an aperture through which an infrared temperature sensor may receive and optionally also emit infrared light.

FIG. 4 illustrates a variant of the apparatus 1, which includes an infrared temperature sensor 23. The infrared sensor 23 is placed on the circuit board 17. An aperture 24 in the EMI shielding 21 is located above the temperature sensor 23. This aperture 24 ensures that IR radiation reaches the temperature sensor 23. Without the aperture or gap 24, IR radiation from the fluid flow 10 in the tube 8 would be blocked by the EMI shielding 21. If the EMI shielding/ electrically conductive layer 21 is a foil, the gap 24 may be obtained by puncturing the foil where the gap 24 is to be located.

The aperture 24 may be, for example, 1 to 5 mm, in particular 1 to 4 mm, and in one embodiment 2 to 3 mm in diameter. Within these ranges, the aperture 24 is sufficiently large to enable proper operation of the infrared temperature sensor 23 but also sufficiently small to maintain efficient EMI shielding of the electrical components.

The infrared temperature sensor 23 may be mounted on the circuit board 17, wherein a light sensitive side 25 of the infrared temperature sensor 23 faces the bottom window 18. The aperture 24 may be covered with the protective coating 22, if it allows IR light transmission. Such a protective coating 22 that allows IR light transmission may be made of, for example, acrylic, silicone, polyurethane or a combination of dielectric materials.

The conductive layer 21 (foil or vapor deposit) may be applied in the shape of an orthogonal crosshatch, comprising a first plurality of parallel metallic traces that intersect at right angles with a second plurality of parallel metallic traces. Alternatively, the conductive layer 21 may be applied in the shape of a diagonal crosshatch comprising a first plurality of parallel metallic traces that intersect diagonally with a second plurality of parallel metallic traces as shown in FIG. 3. This is to ensure EMI shielding of the sensor assembly (i.e., ultrasonic transducers 14, 16, and circuit board 17), whilst allowing easy passage of infrared light. Accordingly, it is preferable to only apply the crosshatch to the window behind which the infrared sensor 23 sits, viz., the bottom window 18. The EMI shielding 21 prevents EMI noise from interfering with the sensor assembly's components 14, 16, 17. When the conductive layer 21 is applied in the shape of a crosshatch (orthogonal or diagonal), the size of the gaps of non-coverage are preferably limited to no more than one-quarter wavelength of the interfering RF signal.

Figure 5:
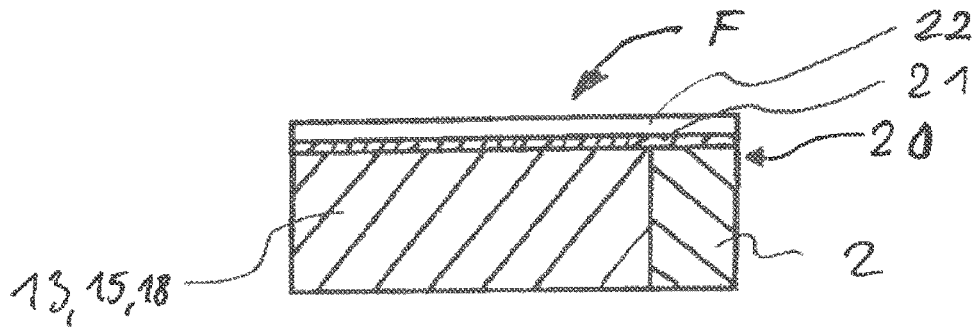
FIG. 5 is a cross section through a window with a layer consisting of a vapor deposited metal and a protective coating placed thereupon.
Figure 6:
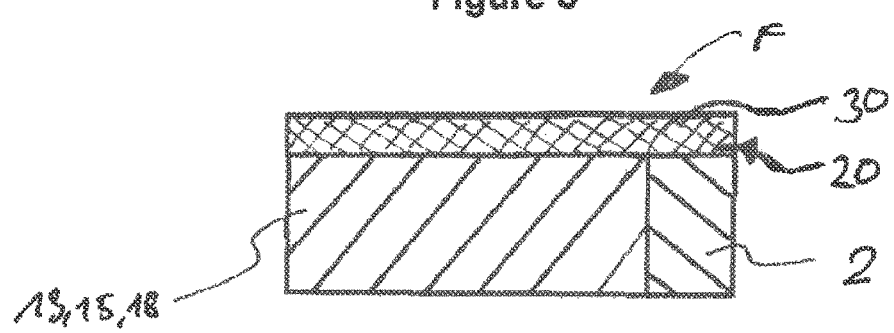
FIG. 6 is a cross section of a window where a layer consisting of metal foil is placed onto the window.

FIG. 5 provides more details on the variant wherein the EMI shielding 21 is a vapor deposited metal. FIG. 6 provides more details on the variant wherein the EMI shielding 30 is a metallic foil.

FIG. 5 shows a cross section through a portion of a window 13, 15 or 18 according to this variant. The EMI shielding 21 is a vapor deposited metal, which is applied on a face side F of the window. The face side F is the side of the window that faces the channel 6. A protective coating 22 made, e.g., of lacquer, covers the vapor deposited metal 21. The vapor deposited metal 21 may be aluminum deposited on the housing 2 and the window 13, 15, 18, such that the vapor deposited metal 21 extends over an electrically grounded portion 20 of the housing 2.

FIG. 6 shows a cross section through a portion of a window 13, 15 or 18 according to this variant. A layer of metal foil 30 is applied on a face side F of the window 13, 15 or 18. The face side F is the side of the window 13, 15 or 18 that faces the channel 6. The metal foil 30 may be copper with an adhesive side, configured to adhere to the housing 2 and the window 13, 15, 18, such that the metal foil 30 extends over an electrically grounded portion 20 of the housing 2.

In one embodiment, the electrically conductive layer 21 can take a different form over one or more of the windows 13, 15 and 18. That is, the electrically conductive layer 21 over window 13 is a metal foil, a vapor deposited metal or a crosshatch pattern of metallic traces, the electrically conductive layer 21 over window 15 is a metal foil, a vapor deposited metal or a crosshatch pattern of metallic traces, and the electrically conductive layer 21 over window 18 is a metal foil, a vapor deposited metal or a crosshatch pattern of metallic traces. For example, in one embodiment, the electrically conductive layer 21 over windows 13 and 15 is a vapor deposited metal, and the electrically conductive layer 21 over window 18 is a crosshatch pattern of metallic traces.

Figure 7:
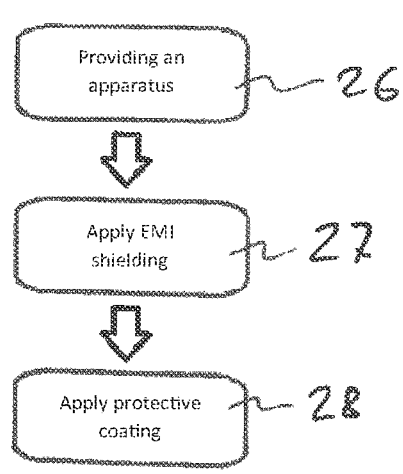
FIG. 7 illustrates three steps of a method for providing an apparatus for fluid flow sensing and bubble detection with a layer of conductive material and a layer of protective material.

FIG. 7 depicts the steps of a method of adapting an apparatus for fluid flow and bubble detection to shield it from EMI. Reference is made to the previous figures. In this method, a first step 26 entails providing an apparatus 1 comprising a housing 2, in which a first sidewall 3, a second sidewall 4 and a bottom wall 5 constitute three walls of a channel 6. The channel 6 is configured to receive a tube 8. The housing 2 further comprises a first window 13 located in the first side wall 3, a second window 15 located in the second side wall 4, a first ultrasonic transducer 14, operable as an ultrasonic transmitter and as an ultrasonic receiver, placed in the housing 2 behind the first window 13, and a second ultrasonic transducer 16, operable as an ultrasonic transmitter and ultrasonic receiver, placed in the housing 2 behind the second window 15. In step 27, an EMI shielding in the form of a layer of electrically conductive material is applied on a face side of the windows facing the channel 6. The windows are completely or partially covered with the layer of electrically conductive material. If they are partially covered, the size of the gaps of non-coverage are preferably limited to no more than one-quarter wavelength of the interfering RF signal.

In embodiments where the layer is a foil, the foil is applied in the second step 27 and the method is finished. In embodiments where the layer is a vapor deposited material deposited in step 27, a third step 28 may consist of applying a protective coating onto the electrically conductive layer.

Those of skill in the art will appreciate that embodiments not expressly illustrated herein may be practiced within the scope of the claims, including that features described herein for different embodiments may be combined with each other and/or with currently known or future-developed technologies while remaining within the scope of the claims. Those of skill in the art will also be enabled to practice various other embodiments of concepts for assessing and/or identifying compatible patient support and patient support mounting devices combinations from the embodiments disclosed herein. Although specific terms are employed herein, they are used in a generic and descriptive sense only and not for purposes of limitation. It is therefore intended that the foregoing detailed description be regarded as illustrative rather than limiting. Furthermore, the advantages described above are not necessarily the only advantages of the disclosure, and it is not necessarily expected that all of the described advantages will be achieved with every embodiment.

The invention claimed is:

1. A fluid flow sensing and bubble detecting apparatus, comprising:
   a housing having two side walls and a bottom wall defining a channel configured to receive a tube through which a conductive fluid flows;
   a window to the channel through a portion of the one or more of the two side walls;
   a fluid flow sensing and bubble detecting electrical sensor assembly positioned in the housing adjacent a side of the window opposite the channel and configured to sense the flow rate of the conductive fluid flowing through the tube and to detect bubbles in the conductive fluid; and an electrically grounded Electro-Magnetic Interference (EMI) shielding layer separate from the fluid flow sensing and bubble detecting electrical sensor assembly and arranged on a surface of the window between at least a part of the sensor assembly and the channel such that the EMI shielding layer protects the sensor assembly from EMI emanating from the conductive fluid flowing through the tube received within the channel.

2. The apparatus of claim 1, wherein the EMI shielding layer is electrically conductive and connected via an electrically conductive path to an electrically grounded portion of the housing.

3. The apparatus of claim 1, wherein the EMI shielding layer is a metal foil, a vapor deposited metal or a crosshatch pattern of metallic traces.

4. The apparatus of claim 1, further comprising a dielectric protective coating covering the EMI shielding layer.

5. The apparatus of claim 1, wherein the sensor assembly comprises at least one pair of ultrasonic transducer elements, wherein each transducer element is electrically isolated from the apparatus's electrical ground and thus is electrically floating.

6. The apparatus of claim 1, wherein the sensor assembly further comprises a temperature sensor.

7. The apparatus of claim 6, wherein the EMI shielding layer has a temperature sensor gap allowing unimpeded temperature measurements by the temperature sensor.

8. A method of monitoring the flow of a biomedical fluid, the method comprising:
   removing the biomedical fluid from a subject during a procedure;
   conveying the biomedical fluid to the system according to claim 1, wherein the conductive fluid comprises the biomedical fluid and flows through the tubing in the channel of the housing; and
   sensing the flow rate of the biomedical fluid through the tubing and detecting the presence of gas bubbles in the biomedical fluid flowing through the tubing using the first and second sensors, wherein the first and second EMI shielding layers minimize noise pick-up by the first and second sensors from the biomedical fluid thereby minimizing false flow rate readings and false bubble detections.

9. A fluid flow sensing and bubble detecting apparatus, comprising:
   a housing having a first side wall, a second side wall and a bottom wall defining three walls of a channel configured to receive a tube through which an electrically conductive fluid flows;
   a first window to the channel through a portion of the first side wall;
   a second window to the channel through a portion of the second side wall;
   a first ultrasonic transducer operable as an ultrasonic transmitter and as an ultrasonic receiver positioned in the housing adjacent a side of the first window opposite the channel;
   a second ultrasonic transducer operable as an ultrasonic transmitter and as an ultrasonic receiver placed positioned in the housing adjacent a side of the second window opposite the channel;
   a circuit board in electrical connection and in signal transferring connection with the first and second ultrasonic transducers, wherein the circuit board is configured to control the first and second ultrasonic transducers as ultrasonic transmitters and receivers, wherein the circuit board is positioned in the housing adjacent a side of the bottom wall opposite the channel;
   a first electrically conductive layer separate from the first and second ultrasonic transducers and located on a side of the first window facing the channel, wherein the first electrically conductive layer is electrically grounded; and
   a second electrically conductive layer separate from the first and second ultrasonic transducers and located on a side of the second window facing the channel, wherein the second electrically conductive layer is electrically grounded.

10. The apparatus of claim 9, further comprising:
    a third ultrasonic transducer operable as an ultrasonic transmitter and as an ultrasonic receiver positioned in the housing behind adjacent the side of the first window opposite the channel; and
    a fourth ultrasonic transducer operable as an ultrasonic transmitter and as an ultrasonic receiver positioned in the housing behind adjacent the side of the second window opposite the channel;
    wherein the first ultrasonic transducer is positioned diagonal to the fourth ultrasonic transducer, and the second ultrasonic transducer is positioned diagonal to the third ultrasonic transducer; and wherein the circuit board is in further electrical connection and in signal transferring connection with the third and fourth ultrasonic transducers, wherein the circuit board is further configured to control the third and fourth ultrasonic transducers as ultrasonic transmitters and receivers.

11. The apparatus of claim 9, further comprising:
    a bottom window to the channel through a portion of the bottom wall.

12. The apparatus of claim 11, further comprising:
    a third electrically conductive layer located on a side of the bottom window facing the channel, wherein the third electrically conductive layer is electrically grounded.

13. The apparatus of claim 12, wherein the first electrically conductive layer, the second electrically conductive layer, and the third electrically conductive layer are conductively connected to an electrically grounded portion of the housing.

14. The apparatus of claim 12, wherein the first electrically conductive layer is a first metal foil, a first vapor deposited metal or a first crosshatch pattern of metallic traces; wherein the second electrically conductive layer is a second metal foil, a second vapor deposited metal or a second crosshatch pattern of metallic traces; and wherein the third electrically conductive layer is a third metal foil, a third vapor deposited metal or a third crosshatch pattern of metallic traces.

15. The apparatus of claim 12, further comprising a dielectric protective coating covering each of the first electrically conductive layer, the second electrically conductive layer, and the third electrically conductive layer.

16. The apparatus of claim 9, wherein the circuit board is essentially planar and oriented parallel to the bottom wall.

17. The apparatus of claim 9, further comprising an infrared temperature sensor mounted on the circuit board, wherein a light sensitive side of the infrared temperature sensor faces the bottom wall.

18. The apparatus of claim 14, further comprising an infrared temperature sensor mounted on the circuit board, wherein a light sensitive side of the infrared temperature sensor faces the bottom wall.

19. A system for minimizing false sensor readings during a procedure performed on a subject, the system comprising:
- a housing defining a channel having two side walls and a bottom wall, and comprising a first window to the channel through a portion of the first side wall, and a second window to the channel through a portion of the second side wall;
- a tubing received in the channel of the housing;
- an electrical sensor assembly configured to sense fluid flow and detect bubbles in a conductive fluid flowing through the tubing, the electrical sensor assembly comprising:
  - a first sensor positioned in the housing on a side of the first window opposite the channel, and
  - a second sensor positioned in the housing on a side of the second window opposite the channel;
- a first electrically grounded Electro-Magnetic Interference (EMI) shielding layer on a surface of the first window; and
- a second electrically grounded EMI shielding layer on a surface of the second window,
- the system being configured such that during the procedure:
  - the conductive fluid flows through the tubing in the channel of the housing outside of the patient,
  - the first and second sensors sense the flow rate of the conductive fluid through the tubing and detect the presence of gas bubbles in the conductive fluid flowing through the tubing, and
  - the first and second EMI shielding layers minimize noise pick-up by the first and second sensors from the conductive fluid to thereby minimize false flow rate readings and false bubble detections.

20. The system according to claim 19, wherein each of the first and second EMI shielding layers extend to a portion of the housing that is electrically grounded.

* * * * *